United States Patent [19]
Cohn

[11] Patent Number: 5,576,316
[45] Date of Patent: Nov. 19, 1996

[54] METHOD FOR INHIBITING TUMOR GROWTH RATE USING CREATINE OR CREATINE ANALOGS

[75] Inventor: Mildred Cohn, Narberth, Pa.

[73] Assignee: University of Pennsylvania, Philadelphia, Pa.

[21] Appl. No.: 416,499

[22] Filed: Apr. 4, 1995

Related U.S. Application Data

[63] Continuation of Ser. No. 25,516, Mar. 2, 1993, abandoned, which is a continuation-in-part of Ser. No. 10,667, Jan. 28, 1993, abandoned.

[51] Int. Cl.$^6$ ............ A61K 31/415; A61K 31/505; A01N 43/54; A01N 43/58
[52] U.S. Cl. ............ 514/218; 514/275; 514/385; 514/386; 514/396; 514/553; 514/561; 514/563; 514/564; 514/579; 514/631; 514/638; 514/646
[58] Field of Search ................ 514/218, 275, 514/385, 386, 396, 553, 561, 563, 564, 579, 631, 638, 646

[56] References Cited

U.S. PATENT DOCUMENTS

| | | | |
|---|---|---|---|
| 5,219,846 | 6/1993 | Bru et al. | 514/118 |
| 5,324,731 | 6/1994 | Kaddurah-Daouk et al. | 514/275 |

*Primary Examiner*—Nathan M. Nutter
*Attorney, Agent, or Firm*—Lahive & Cockfield; Elizabeth A. Hanley

[57] ABSTRACT

A method for inhibiting tumor growth rate using creatine or creatine analogs is described. The creatine or creatine analogs are administered to subjects such that tumor growth rate is inhibited. Pharmaceutical compositions containing the creatine or creatine analogs and packaged products also are described.

6 Claims, 7 Drawing Sheets

METHOD FOR INHIBITING TUMOR GROWTH RATE USING CREATINE OR CREATINE ANALOGS

RELATED APPLICATION

This application is a continuation of application Ser. No. 08/025,516 filed on Mar. 2, 1993 entitled "A Method for Inhibiting Tumor Growth Rate Using Creatine or Creatine Analogs" and now abandoned which is a continuation-in-part of application Ser. No. 08/010,667 filed on Jan. 28, 1993 and now abandoned.

BACKGROUND OF THE INVENTION

New discoveries improving a physician's ability to treat neoplastic diseases, i.e. cancer, are continually being made. For example, superior tumor growth rate inhibiting drugs are being discovered and new therapeutic regimens for concurrent administration of drugs are being designed. Difficulties sometimes are encountered when developing tumor growth rate inhibiting drugs because the drugs have to be capable of performing their function at acceptable levels of toxicity in vivo.

Creatine is a compound which is naturally occurring and is found in mammalian skeletal muscle, brain, and other organs (except for the liver). Creatine can be synthesized relatively easily and is believed to be non-toxic to mammals. Kaddurah-Daouk et al. (WO 92/08456 published May 29, 1992 and WO 90/09192, published Aug. 23, 1990) describe methods of inhibiting the growth, transformation and/or metastasis of mammalian cells using drugs "capable of inhibiting purine metabolic enzyme activity". Examples of drugs described by Kaddurah-Daouk et al. include cyclocreatine, homocyclocreatine, 1-carboxymethyl-2-iminohexahydropyrimidine, guanidino acetate and carbocreatine. Kaddurah-Daouk et al. also studied ten other guanidino-like analogs and concluded that the ten analogs lacked the ability to inhibit the growth, transformation or metastasis of mammalian cells. This conclusion was based on the results of an in vitro assay using known tumor cell lines.

SUMMARY OF THE INVENTION

The present invention pertains to methods of inhibiting tumor growth rate in a subject by administering creatine or creatine analogs to the subject such that tumor growth rate is inhibited. Creatine is a naturally occurring substance alleviating problems associated with toxicity of some presently available, non-naturally occurring anti-tumor or anti-proliferative drugs. The creatine analogs which are part of this invention differ from the group of active cyclocreatine analogs disclosed by Kaddurah-Daouk et al., cited supra, and designated as having tumor growth rate inhibiting properties. The present invention is based, at least in part, on the realization that creatine analogs which did not exhibit anti-tumor properties in accepted in vitro assays using tumor cell lines (such as those described by Kaddurah-Daouk et al., cited supra) may still be active in subjects in vivo. For example, creatine itself did not have tumor growth rate inhibiting activity in in vitro tumor cell line assays yet creatine does have tumor growth rate inhibiting activity in vivo as shown in the examples below. This discovery led to the realization that other creatine analogs which previously had been shown to have no significant activity in vitro against tumor cell lines may be active in vivo especially if the analog is closely structurally related to creatine or cyclocreatine. It is expected that a creatine analog will be active in vivo if the analog has been shown to be active against a tumor cell line in vitro.

The present invention further pertains to compositions for inhibiting tumor growth rate in a subject. The compositions contain creatine or a creatine analog and a pharmaceutically acceptable carrier. The invention also pertains to packaged drugs for treating subjects having tumors or predisposed to the formation of tumors. The packaged drugs include a container holding the creatine or creatine analog along with instructions for administering the same for the purpose of inhibiting the growth rate of a tumor.

DETAILED DESCRIPTION

Figure 1:
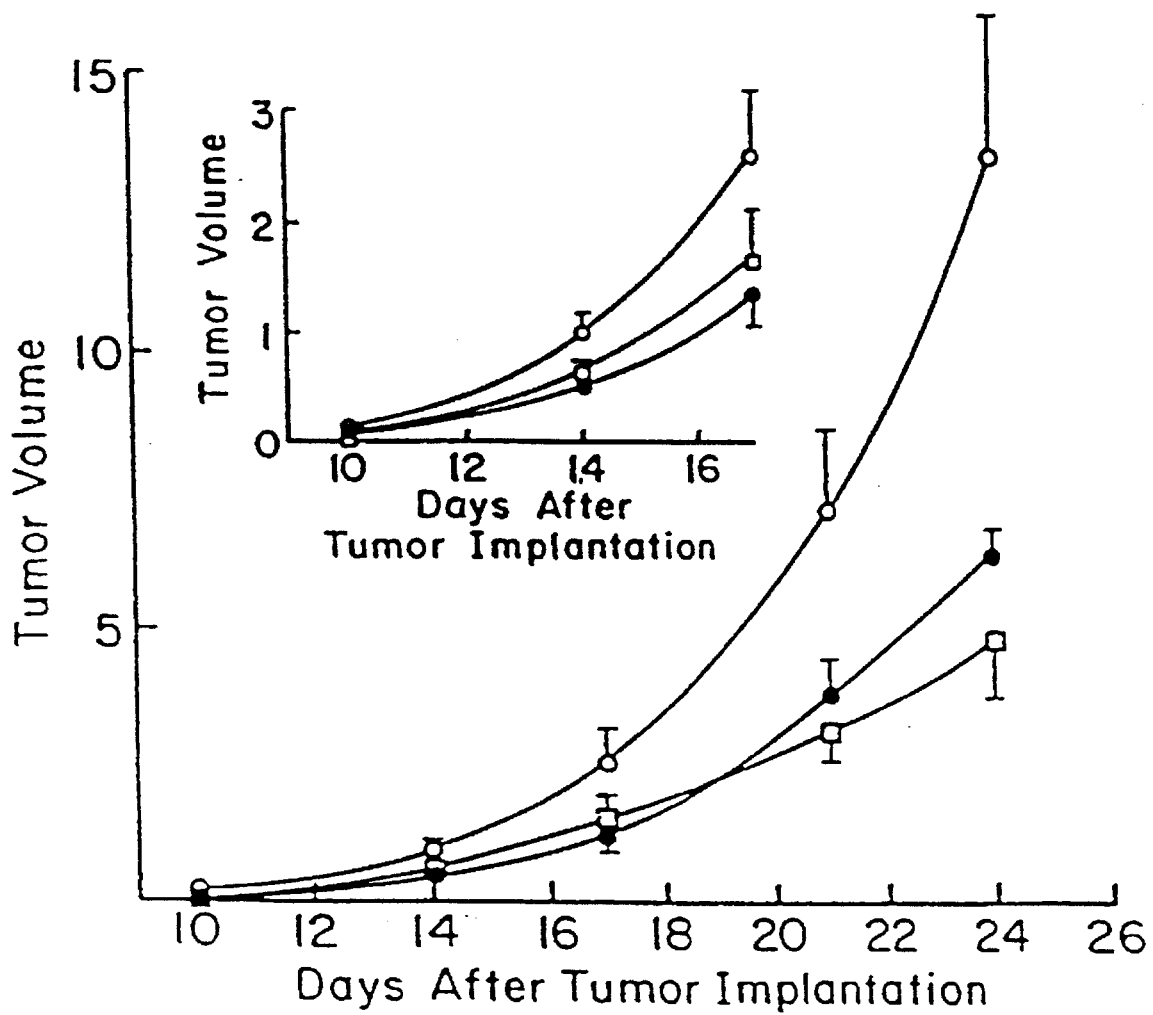
FIG. 1 depicts tumor growth curves for mammary adenocarcinoma Ac33tc for twenty-four days after implantation in female Lewis rats. The symbols are as follows: control (○), 1% cyclocreatine (●), 1% creatine (□). The error bars correspond to SEM values.

The present invention pertains to methods for inhibiting the growth rate of a tumor in a subject. The method includes the administration of a tumor growth rate inhibiting amount of creatine or a creatine analog, described in detail below, to a subject such that the growth rate of a tumor in the subject is inhibited. The creatine or analog thereof also may be administered in the form of a salt. For ease of discussion below, the language "creatine-like compounds" will be used to include creatine, creatine salts, the creatine analogs intended to be part of this invention, and creatine analog salts.

3

The term subject is intended to include living organisms susceptible to having tumors form in or on areas of their body, e.g. mammals. Examples of subjects include humans, dogs, cats, horses, cows, goats, rats and mice. The term subject further is intended to include transgenic species.

The language "inhibiting the growth rate of a tumor" is intended to include prevention of the formation of a tumor, the inhibition of the growth rate of a preexisting tumor and the reduction in size of a preexisting tumor. Creatine and the analogs described herein have both inhibitory and prophylactic effects on tumor formation.

The term tumor is art-recognized and is intended to include tumors whose growth rate is inhibited by creatine or the creatine analogs described herein. As described by Kaddurah-Doauk et al. cited supra, the entire contents of which is expressly incorporated by reference, it is known that creatine kinase is elevated in some types of tumors and it has been described as a tumor-associated marker. At least these tumors are intended to be tumors whose growth rate is inhibited by the method(s) of this invention. Examples of types of tumors include carcinomas, sarcomas, gliomas, and neuroblastomas. Examples of locations on or within the subject where the tumors may form include bladder, testis, head, neck, ovary, uterus, cervix, stomach, bowel and anal canal. Specific types of tumors are discussed within the examples below.

The term administration is intended to include routes of administration which allow the creatine-like compounds to perform their intended function of inhibiting the tumor growth rate in a subject. Examples of routes of administration which may be used include injection (subcutaneous intravenous, parenterally, intraperitoneally, etc.), oral, inhalation, transdermal, and rectal. Depending on the route of administration, the creatine-like compound may be coated with or in a material to protect it from the natural conditions which may detrimentally effect its ability to perform its intended function. The administration of the creatine-like compound is done at dosages and for periods of time effective to significantly reduce the growth rate of tumors or prevent the growth of tumors. Dosage regimes may be adjusted for purposes of improving the therapeutic response of the compound. For example, several divided doses may be administered daily or the dose may be proportionally reduced as indicated by the exigencies of the therapeutic situation.

The language "tumor growth rate inhibiting amount" is intended to include the amount of the creatine-like compound sufficient to prevent tumor growth or significantly reduce tumor growth rate in the subject being treated. A tumor growth rate inhibiting effective amount can be determined on an individual basis and will be based, at least in part, on consideration of the severity of the symptoms to be treated (e.g., the size and number of the tumors) and the activity of the specific analog selected if an analog is being used. Further, the effective amounts of the creatine-like compound may vary according to the age, sex and weight of the subject being treated. Thus, a tumor growth rate inhibiting effective amount of the creatine-like compound can be determined by one of ordinary skill in the art employing such factors as described above using no more than routine experimentation.

Creatine (also known as N-(Aminoiminomethyl)-N-methylglycine, methylglycoamine or N-methyl-guanido acetic acid) is a well-known substance (see *The Merck Index* Ninth Edition, No. 2556 (1976)) and its formula is as follows:

4

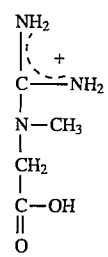

Creatine is present in the muscular tissue, brain and other organs (except liver) of many vertebrates and the naturally occurring product commercially is extracted from meat. The term creatine is intended to include both the isolated naturally occurring form and the chemically synthesized form. Creatine presently is commercially available and further may be chemically synthesized using conventional techniques such as by heating cyanamide with sarcosine (Strecher *Jahresber. Chem.* (1868), 686; cf. Volhard *Z. Chem.* 5,318 (1869); Paulmann, *Arch. Pharm.* 232, 638 (1894); Bergmann et al. *Z. Physiol. Chem.* 173, 80 (1928); and King J. Chem. Soc. (1930), 2374). Pharmaceutically acceptable salts of creatine also are intended to be part of this invention. Pharmaceutically acceptable salts are art-recognized and typically include carboxyl protecting groups which are hydrolyzable under physiological conditions, e.g. sodium, potassium, and hemisulfate.

The language "creatine analog" is intended to include compounds which are structurally similar to creatine, compounds which are art-recognized as being analogs of creatine, and/or compounds which share the same or similar function as creatine. The preferred creatine analogs of this invention are those encompassed by formula (I) set forth below:

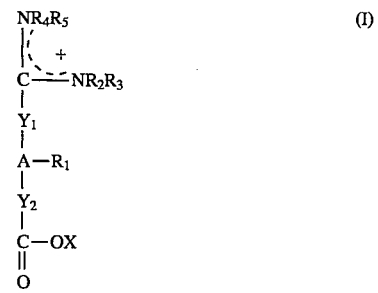

wherein A is selected from the group consisting of N or CH; X is selected from the group consisting of hydrogen and pharmaceutically acceptable salts; $Y_1$ and $Y_2$ are each independently selected from the group consisting of a direct bond, alkylene, alkenylene, alkynylene, alkoxyene and haloalkylene; $R_1$ is selected from the group consisting of hydrogen, alkyl, alkenyl, alkynyl, alkoxy and haloalkyl and $R_2$–$R_5$ are each independently selected from the group consisting of hydrogen,

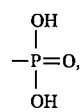

alkyl, alkenyl, alkynyl, alkoxy and haloalkyl, whereby one of the nitrogens in the guanidino moiety alternatively may form a ring structure with A and provided that (I) is not a compound selected from the group consisting of cyclocreatine, homocyclocreatine, 1-carboxymethyl-1-iminohexahydropyrimidine, guanidinoacetate and carbocreatine or salts of the forementioned compounds.

The alkylene, alkenylene, alkynylene, alkyl, alkenyl and alkynyl groups (hereinafter hydrocarbon groups) may have straight or branched chains. The unsaturated groups may have a single site of unsaturation or a plurality of sites of unsaturation. The hydrocarbon groups preferably have up to about ten carbons, more preferably up to about six carbons, and most preferably up to about three carbons. A hydrocarbon group having three carbon atoms or less is considered to be a lower hydrocarbon group. For example, an alkyl group having three carbon atoms or less is a lower alkyl. Examples of lower hydrocarbon groups which may be used in the present invention include methyl, methylene, ethyl, ethylene, ethenyl, ethenylene, ethynl, ethynlene, propyl, propylene, propenyl, propenylene, propynyl, and propynylene. Examples of higher hydrocarbon groups from (four to about ten carbons) include butyl, t-butyl, butylene, butenyl, butenylene, and butynyl, butynylene, nonyl, nonylene, nonenyl, nonenylene, nonynyl, and nonynylene.

The alkoxy, haloalkyl, alkoxyene, and haloalkylene groups (hereinafter substituted hydrocarbon groups) are alkyl or alkylene groups substituted with one or more oxygen or halogen atoms. The alkoxy and haloalkyl groups also may be straight or branched chain and preferably are made up of up to about ten atoms (including carbon, oxygen or halogen), preferably up to about six atoms, and most preferably up to about three atoms. The term halogen is art-recognized and includes chlorine, fluorine, bromine, and iodide. Examples of substituted hydrocarbon groups which are useful within this invention are similar to the examples of the hydrocarbon groups set forth above except for the incorporation of oxygen(s) or halogen(s) into the groups.

The term pharmaceutically acceptable salt (as a possibility for "X" is formula (I) and as it pertains to creatine salts) is intended to include art-recognized pharmaceutically acceptable salts. Typically these salts are capable of being hydrolyzed under physiological conditions. Examples of such salts include sodium potassium, and hemisulfate. The term further is intended to include lower hydrocarbon groups capable of being hydrolyzed under physiological conditions, i.e. groups which esterify the carboxyl moiety, e.g. methyl, ethyl and propyl.

For purposes of this invention, the guanidino moiety of formula I is depicted below:

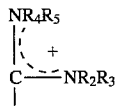

The nitrogens in this moiety may form a ring structure with A. The ring structure may be a single ring or alternatively may be a fused ring system. The preferred ring structures are single rings having five or six ring members such as those present in cyclocreatine—or carbocreatine-like compounds.

The analogs of creatine may be purchased or alternatively may be synthesized using conventional techniques. For example, creatine can be used as the starting material for synthesizing at least some of the analogs encompassed by formula I. Appropriate synthesis reagents, e.g. alkylating, alkenylating or alkynylating agents may be used to attach the respective groups to target sites, e.g. a nitrogen in the guanidino moiety. Alternatively, reagents capable of inserting spacer groups, e.g. $Y_1$ or $Y_2$, may be used to alter the creatine structure. Sites other than the target site are protected using conventional protecting groups while the desired sites are being targeted by synthetic reagents.

If the creatine analog contains a ring structure, i.e. one of the nitrogens in the guanidino moiety forms a ring with "A", then the analog may be synthesized in a manner analogous to that described for cyclocreatine (Wang, T., J. Org. Chem, 39:3591–3594 (1974)). The various "R", "X", and/or "Y" groups may be introduced before or after the ring is formed.

Many creatine analogs have been previously synthesized and described (Rowley et al., J. Am. Chem. Soc. 93:5542–5551 (1971); McLaughlin et al., J. Biol. Chem. 247:4382–4388 (1972); Nguyen, A. C. K., "Synthesis and enzyme studies using creatine analogs", Thesis, Dept. of Pharmaceutical Chemistry, Univ. Calif., San Francisco (1983); Lowe et al., J. Biol. Chem, 225:3944–3951 (1980); Roberts et al., J. Biol. Chem. 260:13502–13508 (1985); Roberts et al., Arch, Biochem. Biophys. 220:563–571 (1983); and Griffiths et al., J. Biol. Chem. 251:2049–2054 (1976)). The contents of all of the forementioned references are expressly incorporated by reference. Further to the forementioned references, Kaddurah-Daouk et al. (WO92/08456) also provide citations for the synthesis of a plurality of creatine analogs (see Examples 2 and 3 including Table 4). The contents of the entire Kaddurah-Daouk et al. published patent application including the contents of any references cited therein also are expressly incorporated by reference.

The present invention further pertains to compositions for inhibiting tumor growth rate including the creatine-like compounds and a pharmaceutically acceptable carrier. The creatine analogs included in the compositions of the present invention preferably are those encompassed by formula (I) which is as described above. The language "tumor growth rate inhibiting amount" also is used as defined above.

The language pharmaceutically acceptable carrier is intended to include substances capable of being coadministered with the creatine-like compound and which allows the active ingredient to perform its intended function of inhibiting tumor growth rate. Examples of such carriers include solvents, dispersion media, delay agents an the like. The use of such media and agents for pharmaceutically active substances is well known in the art. Any conventional media and agent compatible with the creatine-like compound may be used within this invention.

The creatine-like compounds of this invention may be administered alone or in a pharmaceutically acceptable carrier. Further, the compounds may be administered as a mixture of creatine-like compounds which also may be in a pharmaceutically acceptable carrier. The creatine-like compounds even further may be coadministered with other different art-recognized anti-tumor or anti-neoplastic agents.

The present invention further pertains to packaged drugs for treating subjects for the inhibition of tumor growth rate. The package includes a container holding creatine or creatine analogs (preferably those analogs encompassed by formula I) and instructions for administering the creatine or creatine analog to a subject for the inhibition of tumor growth rate in the subject. Examples of containers useful in the packages of this invention include vials, syringes, etc. The instructions would contain dosage information for administering the active ingredient as described above.

The following invention is further illustrated by the following examples which should in no way be construed as being further limiting. The contents of all references and published patent applications cited throughout this application are hereby incorporated by reference. The following methodology described in the Materials and Methods section was used throughout the examples set forth below.

Materials and Methods
Animals and Tumors

Tumors in inbred rats used in these experiments include 13762A in Fischer 344 female rats, Ac33tc in Lewis female rats, and MCI in Lewis male rats. The tumors designated 13762A (Segaloff, A., *Recent Prog. Hormone Res.* (1966) 22:351–374) and Ac33tc are both metastasizing mammary tumors. Ac33tc was derived from the tissue culture of a tumor which arose after the treatment of rats with the anticancer compound dimethyl-β-aziridinoproprionamide (Miller, E. E. et al., *Proc. Am. Soc. Cancer Res.* (1967) 8:182; and Miller, E. E. et al., Jonathan E. Rhoads Eightieth Birthday Symposium (1989) pp. 330–333). The original tumor was not metastatic, whereas the one derived from its tissue culture metastasizes to the regional lymph node and lungs. MCI (Rogers, G. W. et al., *J. Surg. Oncol.* (1977) 9:307–311) is a sarcoma induced in Lewis rats by injection of methylcholanthrene. The Fischer 344 rats were purchased from the National Cancer Institute (NCI), Frederick Cancer Research and Development Center, Frederick, Md. The Lewis rats for carrying tumors were bred in a closed animal colony, and additional rats were purchased when needed from Harlan-Sprague Dawley. All rats used weighed 100–150 grams.

Six week old weaning athymic NCR-NU mice were also obtained from the NCI in Frederick, Md. The neuroblastoma cell lines used were obtained from the laboratory of Dr. Roger Kennett of the University of Pennsylvania. Two lines were investigated, IMR-5 (Balaban-Malenbaum, G. et al., *Science* (1977) 198:739–741) a subclone of IMR-32 (Tumilowicz, J. J. et al., *Cancer Res.* (1970) 30:2110–2118) from the Institute of Medical Research, Camden, N.J., and CHP-134 derived in the research laboratories of the Children's Hospital of Philadelphia by Dr. Harvey Schlesinger.

Implantation of Tumors

To obtain 13762A cells for subcutaneous transplants, 13762A ascites tumor was grown by injecting $1-2\times10^7$ cells in RPMI medium interperitoneally in female Fischer 344 rats and the ascites cells were harvested after one week. The ascites tumor 13762A was adapted to this growth form from the solid tumor 13762NF (Segaloff, A., supra.) supplied by the A. E. Bogden laboratory of the Mason Research Institute, Worcester, Mass. The tumors transplanted into Lewis rats (Ac33tc and MCI) were maintained by trocar transplants as solid tumors, and single cell suspensions were prepared in Hank's balanced salt solution by forcing minced tumor tissue fragments through a 40 mesh stainless steel sieve. The implantation of all rat tumors was made subcutaneously in a volume of 0.5 ml of Hank's balanced salt solution with $0.5\times10^6$ live cells, based on Trypan Blue dye exclusion. All transplants were made using sterile technique.

The neuroblastoma cells were cultured in 1350 ml flasks with modified Dulbecco medium containing 10% fetal calf serum. They were maintained in a humidified atmosphere of 92% air and 8% $CO_2$. At 90% confluence, the cells were harvested with the addition of the sodium salt of ethylenediamine tetraacetic acid (EDTA). For the athymic mice, 0.6 to $0.8\times10^7$ neuroblastoma cells were injected subcutaneously on each side of the lower back.

Diets of Rats Used in Examples

Cyclocreatine was synthesized as described by Wang (Wang, T., *J. Org. Chem.* (1974) 39:3591–3594) and creatine was purchased from Sigma Chemical Co., St. Louis, Mo. The rats were fed Purina Lab Chow RC 50001M (Buckshire Feeds, Lansdale, Pa. ad libitum with no addition or admixed with cyclocreatine (1% by weight) or creatine (1, 2, 5 or 10% by weight). Unless otherwise specified the food in the form of chow meal was fed to the rats from standard glass food dishes. In some examples, the compounds were incorporated with the same chow meal into pellets by Dyets Inc., Bethlehem, Pa. After eating lab chow pellets for two or three weeks after arrival in the lab facility, the mice were fed ground Purina Mouse Chow 5015 with either no addition or admixed with 1% cyclocreatine or 5% creatine. They were housed in filter-top cages.

Evaluation of Tumor Growth

Measurements of tumor size were made in three dimensions, $d_1 \times d_2 \times d_3$, with centimeter calipers using the methodology described by Lo et al. (*Cancer Chemother.* (1973) 57:245–250) at 3–4 day intervals. The hair was shaved from the tumor area to facilitate measurements. Calculations of tumor volume were made by multiplying the product of the three dimensions by $\Pi/6$. Standard deviations were used to obtain the SEM of each experimental group.

EXAMPLE 1

The Tumor Growth Inhibiting Effect of Creatine and Cyclocreatine on Ac33tc Tumors Implanted in Lewis Rats Rat mammary adenocarcinoma Ac33tc tumors were implanted in Lewis rats as described above in the Materials and Method Section. Tumors developed three to six days after implantation in all groups. FIG. 1 depicts the average volumes of the subcutaneously implanted Ac33tc tumors of three groups of rats (the control group, the group with 1% creatine, and the group with 1% cyclocreatine added to the diet) shown as a function of time over a period of twenty-four days after implantation. Each group of rats had three rats. Cyclocreatine depressed the growth over the time course by approximately 50% (range 46–54) and creatine also depressed the growth approximately 50% (range 37–65). Repeated experiments with this tumor gave similar results.

EXAMPLE 2

The Effect of the Dose of Creatine on Ac33 Tumors Implanted in Lewis Rats

Figure 2:
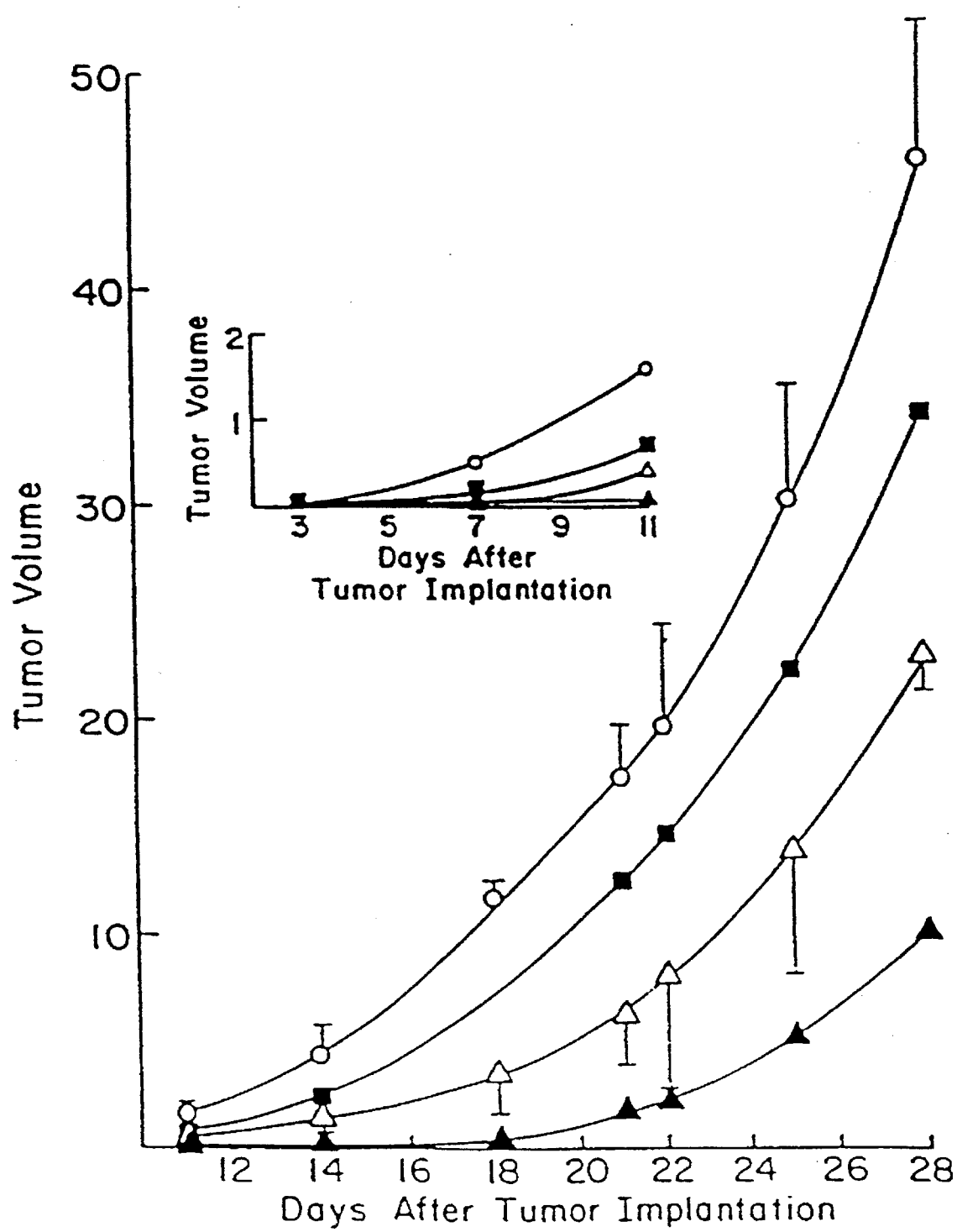
FIG. 2 depicts dose-response growth curves for tumor Ac33tc for twenty-eight days after implantation in Lewis female littermates. The symbols are as follows: control (○), 2% creatine (■), 5% creatine (△); 10% creatine (▲).
Figure 3:
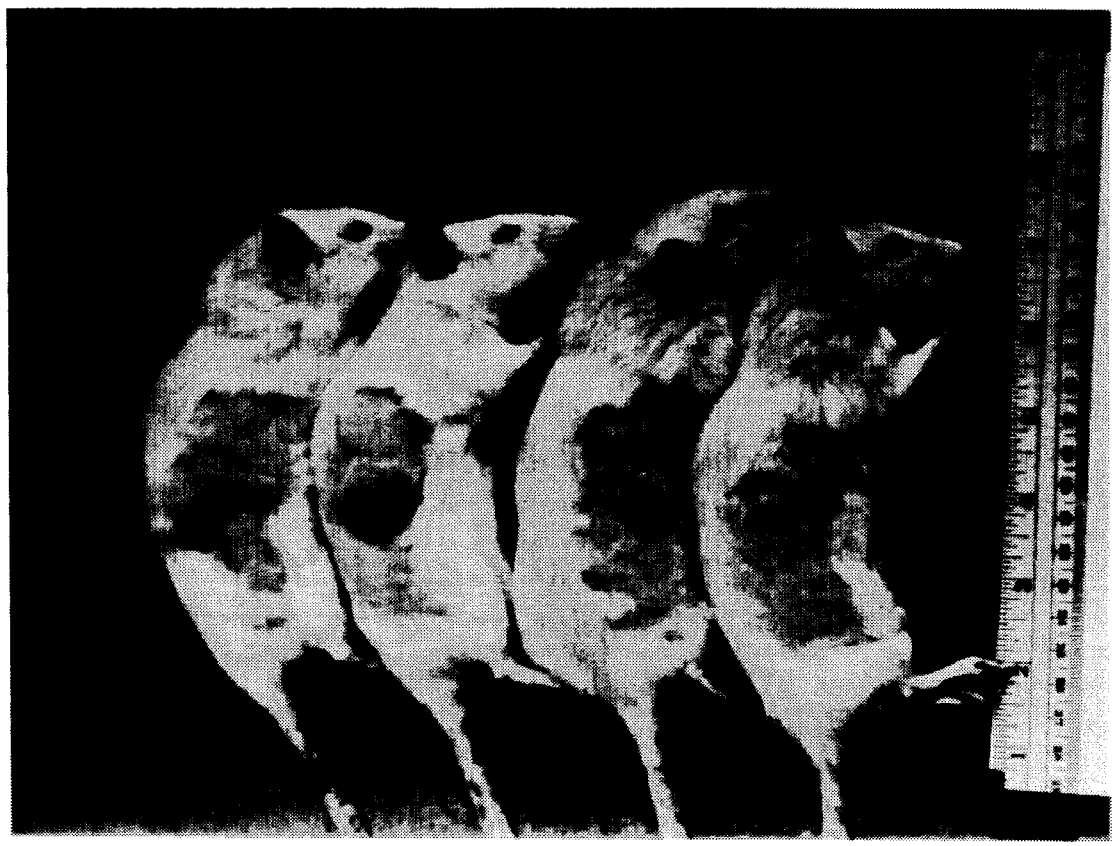
FIG. 3 is a photograph depicting tumor growth inhibition by creatine in the rats used to generate the dose-response growth curves shown in FIG. 2. The photograph was taken on day fifteen.

Further experiments were conducted to study the effect of the dose on tumor growth. A dose-response experiment was conducted using groups containing Lewis rats from the same litter (littermates). Doses of creatine of 2, 5 and 10% of the diet were studied. Two rats were in each group except for the 10% creatine group in which one rat was used. The increasing inhibition of the growth rate of the subcutaneously implanted Ac33tc tumor with increasing creatine level in the diet is shown in FIG. 2. The inhibition of growth by 10% creatine in the diet was almost 90% at twenty-two days after implantation. The urine of rats fed 10% creatine in the diet appeared milky probably due to the excretion of excess insoluble creatine. Rats fed 5% creatine in the diet had a small amount of insoluble material suspended in the urine. One of the rats fed 2% creatine died accidentally on day fifteen. The results on inhibition of tumor growth were striking as shown in the accompanying photograph (FIG. 3).

EXAMPLE 3

Figure 4:
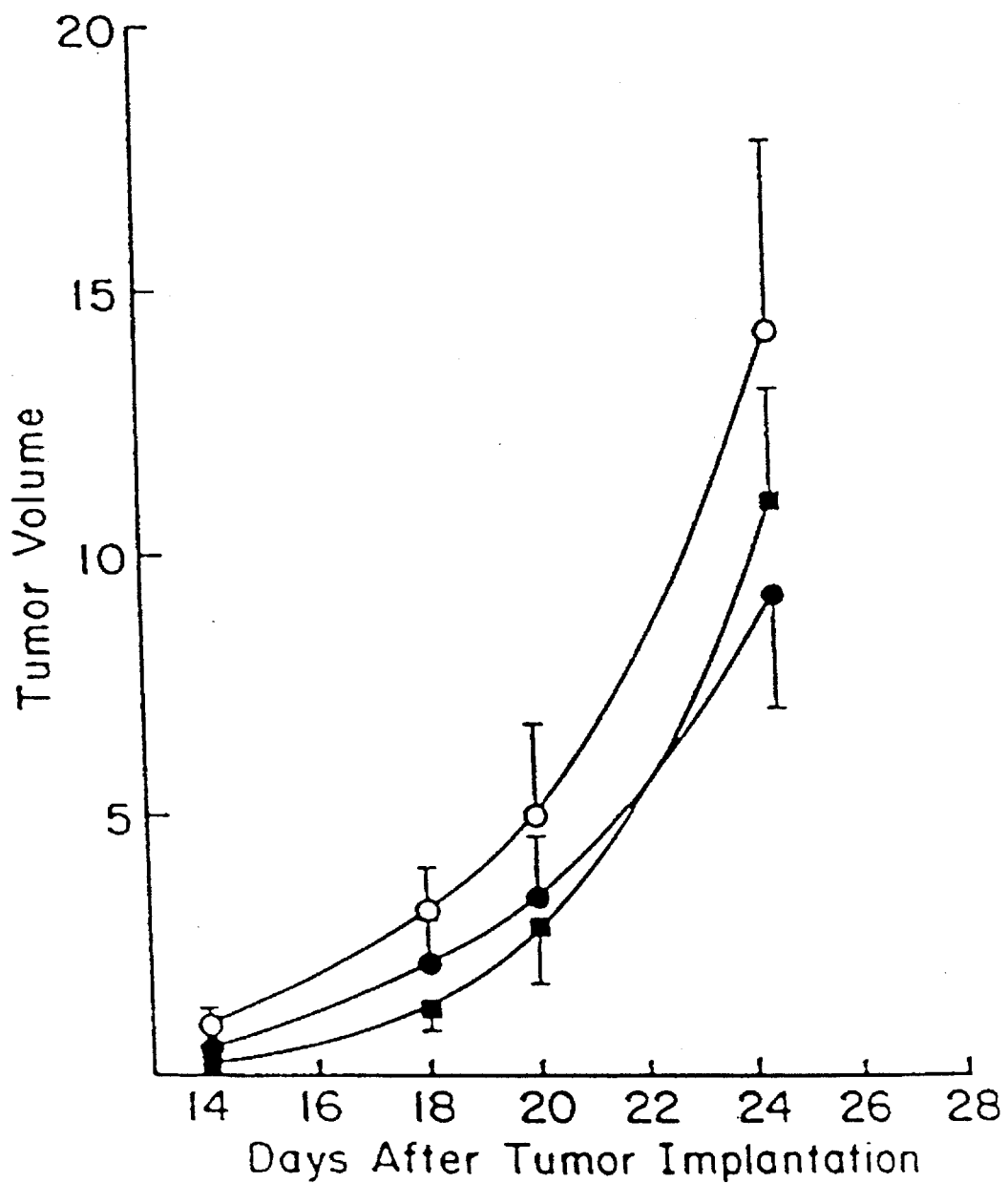
FIG. 4 depicts tumor growth curves for mammary adenocarcinoma 13762A for twenty-five days after implantation in Fischer 344 female littermates. The symbols are as follows: control (○); 1% cyclocreatine (●); and 2% cyclocreatine (■).

The Tumor Growth Inhibiting Effect of Creatine and Cyclocreatine on Mammary Tumors 13762A Implanted in Fischer Rats The tumor growth inhibiting effect of cyclocreatine and creatine also were investigated for the mammary tumor 13762A implanted in Fischer rats. Six Fischer 344 female littermates were in each group. There was a slight delay in tumor development on the experimental diets. The first two tumors appeared in the control group on day seven after implantation and all six had developed on day twelve. One tumor was palpable on day six and all six on day fourteen for the 1% cyclocreatine group. One tumor was observed on day seven and all six on day fourteen for the 2% creatine group. As shown in FIG. 4, 1% cyclocreatine and 2% creatine had similar inhibitory effects on growth rate within experimental error at twenty-five days, 1% cyclocreatine inhibited approximately 35% of tumor growth and 2% creatine inhibited 30% of tumor growth but at 20 days 1% cyclocreatine inhibited 33% of tumor growth and 2% creatine inhibited 43% of tumor growth.

EXAMPLE 4

The Tumor Growth Inhibiting Effect of Creatine and Cyclocreatine on MCI Sarcoma Implanted in Lewis Rats Another type of tumor, the MCI sarcoma was implanted in Lewis male littermates using the methodology described above in the Materials and Method Section. There were six rats in each group and each group was fed experimental diets in the form of pellets containing 1% cyclocreatine or 1% or 5% creatine. All rats had developed tumors at day ten after implantation. Within experimental error, 1% cyclocreatine and 1% creatine were equally effective. The results for the 5% creatine diet did not differ significantly from the 1% creatine unlike the results with the Ac33tc mammary tumor. There was a trend for the creatine to be more effective at earlier times. For example, at sixteen days after implantation, the 1% creatine diet yielded approximately 53% inhibition and the 1% cyclocreatine 41% inhibition but at twenty days after implantation, inhibition was approximately 30% for creatine and 26% for cyclocreatine.

EXAMPLE 5

Figure 5:
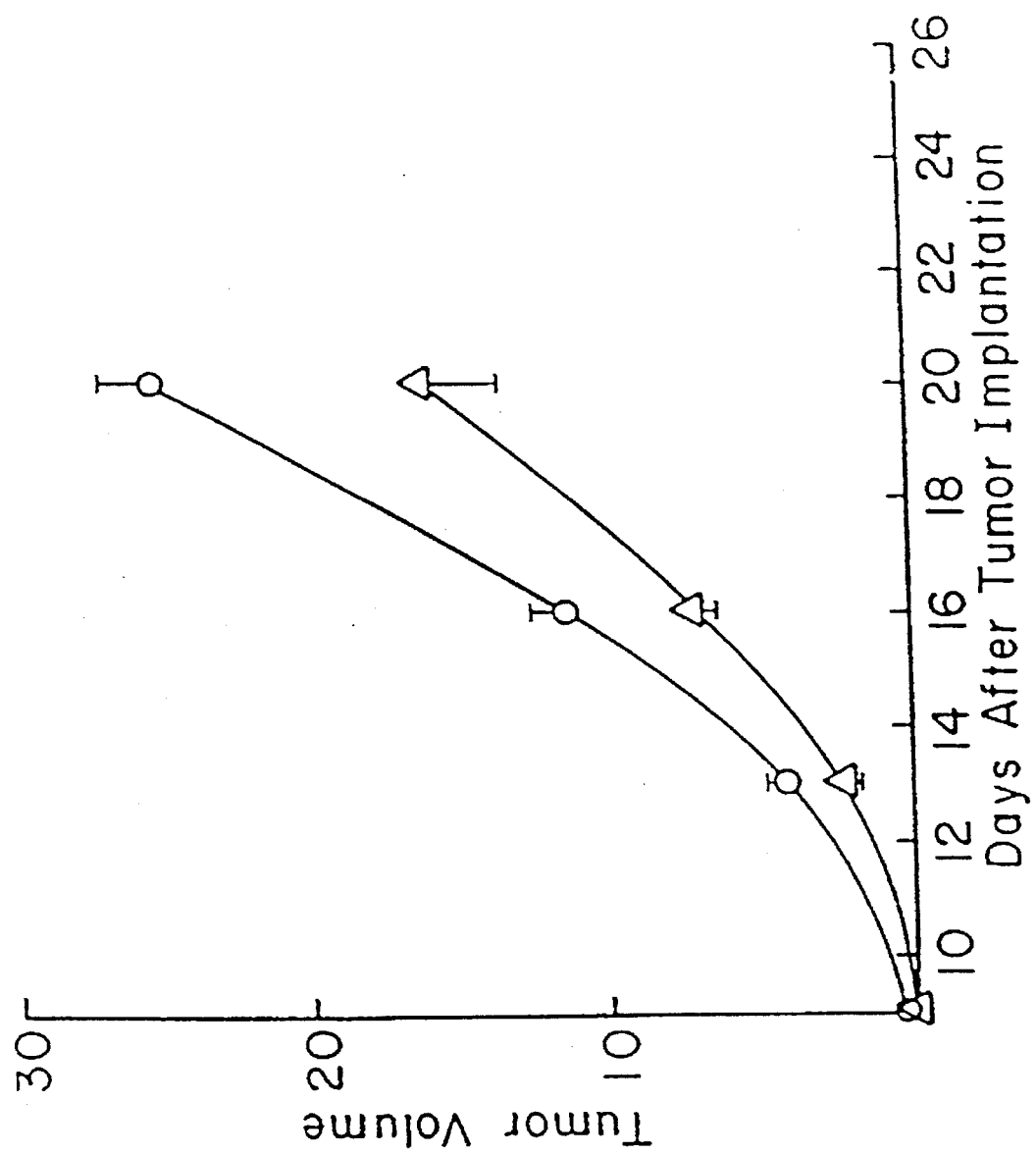
FIG. 5 depicts tumor growth curves for rat sarcoma MCI in Lewis male littermates for twenty days after implantation with a 5% creatine diet initiated six days after implantation when the tumors became palpable. The symbols were as follows: control (○) and 5% creatine (△).

The Tumor Growth Inhibiting Effect of Creatine on Preexisting MCI Sarcoma Implanted in Lewis Rats The effect of feeding 5% creatine after the tumor appeared rather than at the time of implantation was examined with MCI sarcoma using Lewis rats. The tumor growth curves in FIG. 5 show the average volumes of six tumors in the control group and the average volumes of eight tumors in the group fed 5% creatine beginning with the sixth day after implantation when the tumors first appeared and continued until twenty days after implantation. The creatine diet caused approximately 40% inhibition.

EXAMPLE 6

The Tumor Growth Inhibiting Effect of Creatine and Cyclocratine on Human Neuroblastoma Tumors Implanted in Athymic Nude Mice The efficacy of dietary cyclocreatine and creatine as inhibitors of human neuroblastoma tumor growth rate was tested in athymic nude mice. Three groups with four mice in each group were implanted with two injections of CHP-134 cells, one on each side of the lower back in each mouse. The effect of 5% creatine and 1% cyclocreatine in diets, initiated at the time of implantation, was most strikingly reflected in the delay in the development of tumors. Four tumors formed from the eight injections in the four rats of the control group as of day nineteen after implantation. Two tumors formed from the eight injections in the four rats of the cyclocreatine group as of day nineteen after implantation. Two tumors formed from the six injections in the three rats of the creatine group as of day nineteen after implantation. The tumor formation also was examined on day thirty-eight and the results were as follows: six tumors formed in the control group and three tumors in each of the cyclocreatine and creatine groups. Eventually all of the rats developed tumors corresponding to each injection.

EXAMPLE 7

Figure 6:
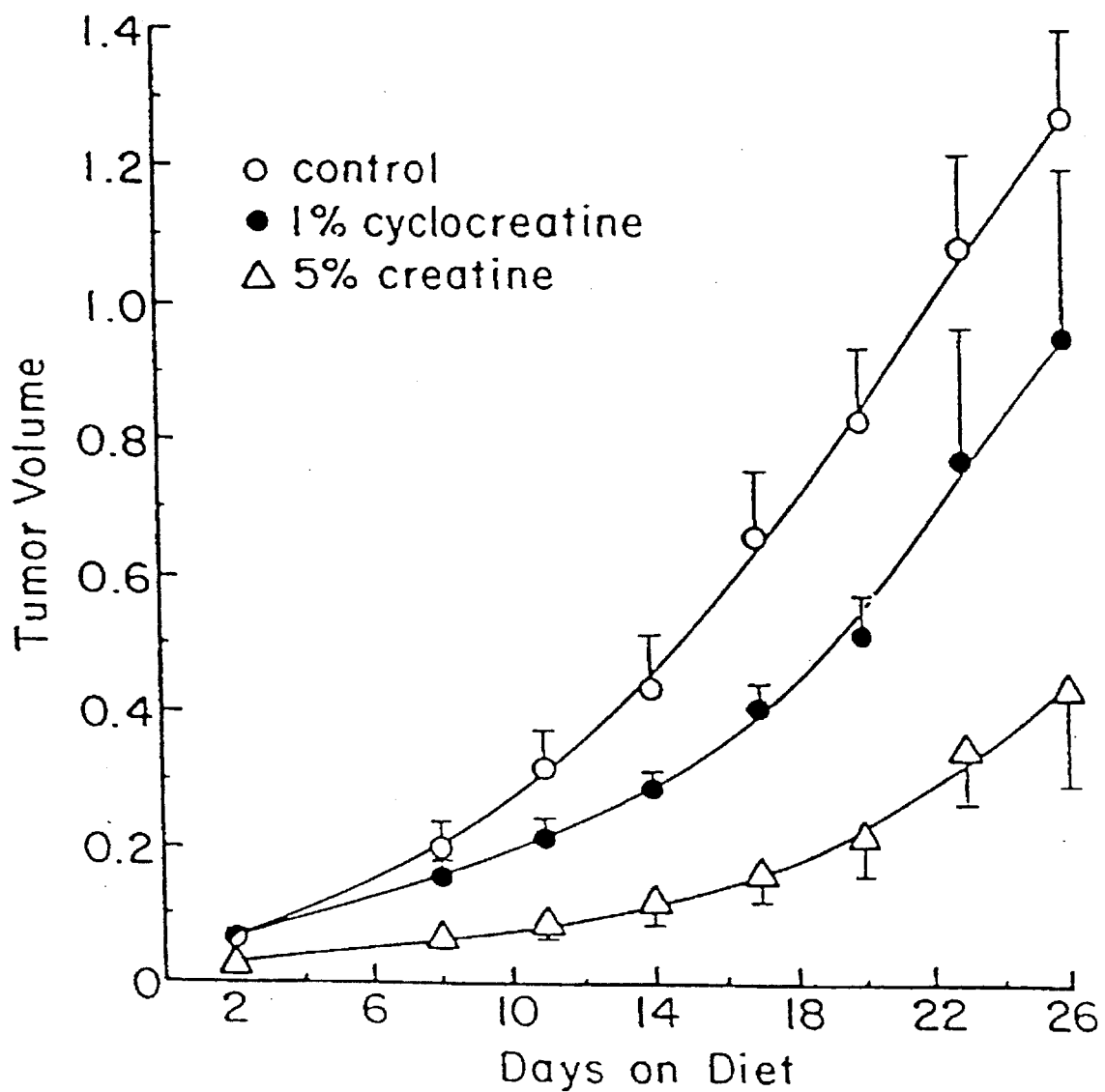
FIG. 6 depicts tumor growth curves (volume versus days on diet) for athymic mice implanted with human neuroblastoma cells (CHP-134). Growth curves were plotted for individual tumors and tumor volumes at three day intervals (from 2 to 26 days) were taken from the individual curves and averaged for each group to obtain the values of tumor volume shown in the figure for control, creatine-fed and cyclocreatine-fed, respectively. The symbols are as follows: control (○); 1% cyclocreatine (●); and 5% creatine (△).

The Tumor Growth Inhibiting Effect of Creatine and Cyclocreatine on Preexisting Tumors in Athymic Nude Mice Derived from CHP-134 Neuroblastoma Cells The experimental design was modified in a second experiment with the CHP-134 neuroblastoma cell line. To ensure that a sufficient number of tumors would be available in each of the three groups for statistically significant analysis, the mice were not fed the experimental diets until tumors had appeared. Thus, each group (control, 1% cyclocreatine-fed and 5% creatine-fed) consisted of eight tumors. The tumor volume of each individual tumor was plotted as a function of days on the diet. The values of the tumor volume of each group plotted in FIG. 6 are averages of the sizes of individual tumors in each group, taken from the volume-time curves of the individual tumors on the days indicated. The number of tumors averaged were as follows: control group 8 (days 2–20), 7 (days 23, 26), cyclocreatine group 8 (days 2–14), 6 (days 17–20), 4 (days 23, 26); creatine group 8 (days 2–20), 7 (day 23) and 6 (day 26). As shown in FIG. 6, the average growth rate over twenty-six days of feeding was inhibited 33% (range 21%–45%) by the cyclocreatine and 71% (range 66%–78%) by creatine.

EXAMPLE 8

Figure 7:
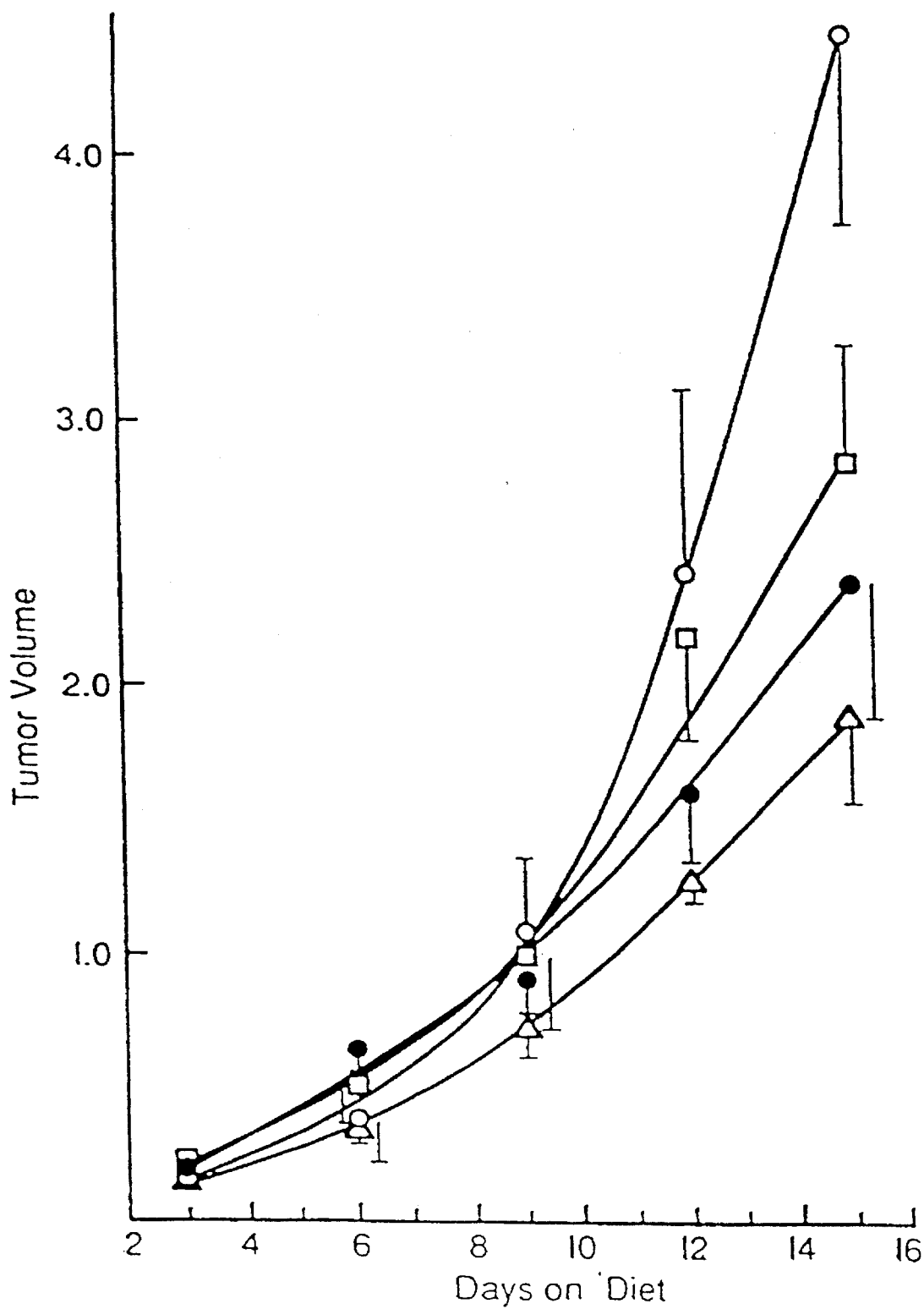
FIG. 7 depicts tumor growth curves (volume versus days on diet) for athymic mice for fifteen days after implantation of neuroblastoma cells (IMR-5) (six from day 0 to 15 and four on day 15). The symbols are as follows: control (○); 1% cyclocreatine (●); 1% creatine (□); 5% creatine (△).

The Tumor Growth Inhibiting Effect of Creatine and Cyclocreatine on Preexisting Tumors in Athymic Nude Mice Derived from IMR-5 Neuroblastoma Cells A similar experiment to that described in Example 7 was conducted using the neuroblastoma cell line IMR-5 with four groups of athymic mice: 1) control 2) 1% cyclocreatine-fed 3) 1% creatine-fed and 4) 5% creatine-fed. There were four animals in each group, each animal with two tumors and the experimental diets were initiated when the tumors appeared. The values of tumor volume plotted in FIG. 7 are averages obtained from volume-time curves of individual mice as described in Example 7 above. The number of tumors averaged were as follows: control group 7; cyclocreatine groups 8 (day 3), 6 (days 6, 9), 5 (day 12); 1% creatine group 8; 5% creatine groups 6 (days 3–12), 4 (day 15). Inhibition of the tumor growth rate for the IMR-5 tumor increased with time. The percent inhibition from day 9 to day 12 ranged from 10 to 36 (1% creatine group), 16 to 46 (1% cyclocreatine group) and from 33 to 57 (5% creatine group). At the same concentration in the diet (1%) cyclocreatine was more effective than creatine but 5% creatine in the diet was most effective. Several mice in the cyclocreatine and 5% creatine group died accidentally on day thirty-two.

EQUIVALENTS

Those skilled in the art will recognize, or be able to ascertain using no more than routine experimentation, many equivalents to the specific embodiments of the invention described herein. Such equivalents are intended to be encompassed by the following claims.

We claim:

1. A method for inhibiting the growth rate of a tumor in a mammal, comprising:

administering to a subject a tumor growth rate inhibiting amount of creatine such that the growth rate of a tumor in the subject is inhibited.

2. The method of claim 1 wherein the subject is a mammal.

3. The method of claim 2 wherein the subject is human.

4. The method of claim 1 wherein the tumor is a mammary tumor.

5. The method of claim 1 wherein the tumor is a sarcoma.

6. The method of claim 1 wherein the tumor is a neuroblastoma.

* * * * *